(12) United States Patent
Cage et al.

(10) Patent No.: US 9,498,226 B2
(45) Date of Patent: Nov. 22, 2016

(54) EMBOLIC COIL DELIVERY SYSTEM

(75) Inventors: Logan Michael Cage, Bloomington, IN (US); Sarah Elizabeth Reeves, Bloomington, IN (US)

(73) Assignee: Cook Medical Technologies, LLC, Bloomington, IN (US)

( * ) Notice: Subject to any disclaimer, the term of this patent is extended or adjusted under 35 U.S.C. 154(b) by 758 days.

(21) Appl. No.: 13/596,599

(22) Filed: Aug. 28, 2012

(65) Prior Publication Data

US 2013/0072961 A1 Mar. 21, 2013

Related U.S. Application Data

(60) Provisional application No. 61/535,553, filed on Sep. 16, 2011.

(51) Int. Cl.
*A61F 2/06* (2013.01)
*A61B 17/12* (2006.01)

(52) U.S. Cl.
CPC ..... *A61B 17/12113* (2013.01); *A61B 17/1214* (2013.01); *A61B 2017/1205* (2013.01)

(58) Field of Classification Search
CPC .......... A61F 2/962; A61F 2/966; A61F 2/97; A61F 2002/9665; A61B 2017/1205; A61B 2017/12054; A61B 17/12022; A61B 17/12113; A61B 17/12118; A61B 17/1214; A61B 17/12145; A61B 17/1215; A61B 17/12154; A61B 2017/12127; A61B 17/1254
USPC ....... 623/1.11, 1.12; 606/108, 194, 200, 191
See application file for complete search history.

(56) References Cited

U.S. PATENT DOCUMENTS

| | | | | |
|---|---|---|---|---|
| 5,312,415 A | * | 5/1994 | Palermo | A61B 17/12022 606/108 |
| 5,735,859 A | * | 4/1998 | Fischell et al. | 606/108 |
| 5,824,041 A | * | 10/1998 | Lenker | A61F 2/91 606/195 |
| 7,972,342 B2 | | 7/2011 | Gandhi et al. | |
| 2002/0026217 A1 | * | 2/2002 | Baker et al. | 606/223 |
| 2002/0032459 A1 | * | 3/2002 | Horzewski | A61B 17/3439 606/198 |
| 2007/0083226 A1 | * | 4/2007 | Buiser | A61B 17/12022 606/200 |
| 2008/0027482 A1 | | 1/2008 | Sekido et al. | |
| 2010/0152650 A1 | | 6/2010 | Schrodt | |
| 2011/0022003 A1 | | 1/2011 | Tekulve | |

OTHER PUBLICATIONS

Cook Medical, Amplatz Vascular Obstruction Device, 2011, pp. 1-2.

* cited by examiner

*Primary Examiner* — Jonathan Miles
*Assistant Examiner* — Kankindi Rwego
(74) *Attorney, Agent, or Firm* — Liell & McNeil

(57) ABSTRACT

An embolic coil delivery system includes a flexible elongate body having a distal segment. An embolic coil is loaded on the flexible elongate body at the distal segment and contacts an outer surface of the flexible elongate body. The embolic coil delivery system also includes a delivery catheter sized to advance over the flexible elongate body during an embolic coil delivery procedure, wherein a distal segment of the delivery catheter contacts the embolic coil during the embolic coil delivery procedure.

16 Claims, 3 Drawing Sheets

EMBOLIC COIL DELIVERY SYSTEM

RELATION TO OTHER PATENT APPLICATION

This application claims priority to provisional patent application 61/535,553, filed Sep. 16, 2011, with the same title.

TECHNICAL FIELD

The present disclosure relates generally to an embolic coil delivery system, and more particularly to a system for loading an embolic coil on an outer surface of a flexible elongate body and advancing a delivery catheter over the flexible elongate body to contact and unload the embolic coil.

BACKGROUND

Embolization procedures are designed to create an artificial blockage within a vessel to block blood from flowing downstream from the blockage. These procedures are used to treat several conditions, including, for example, aneurysms, hemorrhages, and lesions or growths. Specifically, for example, an embolic device may be used to occlude blood flow to an aneurysm and, thus, reduce the risk of the aneurysm rupturing and producing internal hemorrhaging. Embolic devices may include physical barriers, such as coils, balloons, chemicals, and the like. According to one type of embolization procedure, a plurality of embolic coils are delivered to the embolization site. These coils may vary in stiffness, such that a stiffer coil may provide a strong radial force to maintain the position of the artificial blockage, while a softer coil may be used as packing material to occupy space at the blockage.

During an embolic coil delivery procedure, the one or more embolic coils are typically delivered to the embolization site in the vasculature of a patient through the use of a catheter delivery system. Specifically, the embolic coils are loaded into the lumen of a catheter and the catheter is inserted into the vasculature such that the distal end of the catheter is proximate the embolization site. The embolic coils are then advanced through the lumen of the catheter using a pusher wire or pressurized fluid until the coils exit the distal end of the catheter. Unfortunately, this delivery procedure suffers drawbacks, including those caused by the resistance created by the one or more coils loaded into the catheter lumen. For example, this resistance to the force created by the pusher wire or pressurized fluid may lead to procedural complications, including imprecise positioning of the embolic coils within the patient vasculature.

The present disclosure is directed toward one or more of the problems set forth above.

SUMMARY OF THE DISCLOSURE

In one aspect, an embolic coil delivery system includes a flexible elongate body having a distal segment. An embolic coil is loaded on the flexible elongate body at the distal segment and contacts an outer surface of the flexible elongate body. The embolic coil delivery system also includes a delivery catheter sized to advance over the flexible elongate body during an embolic coil delivery procedure, wherein a distal segment of the delivery catheter contacts the embolic coil during the embolic coil delivery procedure.

In another aspect, a preloaded wire guide for an embolic coil delivery system includes a mandril wire guide having a distal segment. An embolic coil is loaded on the mandril wire guide at the distal segment and contacts an outer surface of the flexible elongate body. A delivery sheath is positioned over the embolic coil.

In yet another aspect, a method of delivering an embolic coil to a delivery site within a patient vessel includes loading the embolic coil around an outer surface of a distal segment of a flexible elongate body. The distal segment of the flexible elongate body is advanced through the patient vessel to the delivery site, and the embolic coil is unloaded from the flexible elongate body at least in part by advancing a delivery catheter over the flexible elongate body and contacting the embolic coil with a distal segment of the delivery catheter.

DETAILED DESCRIPTION

Figure 1:
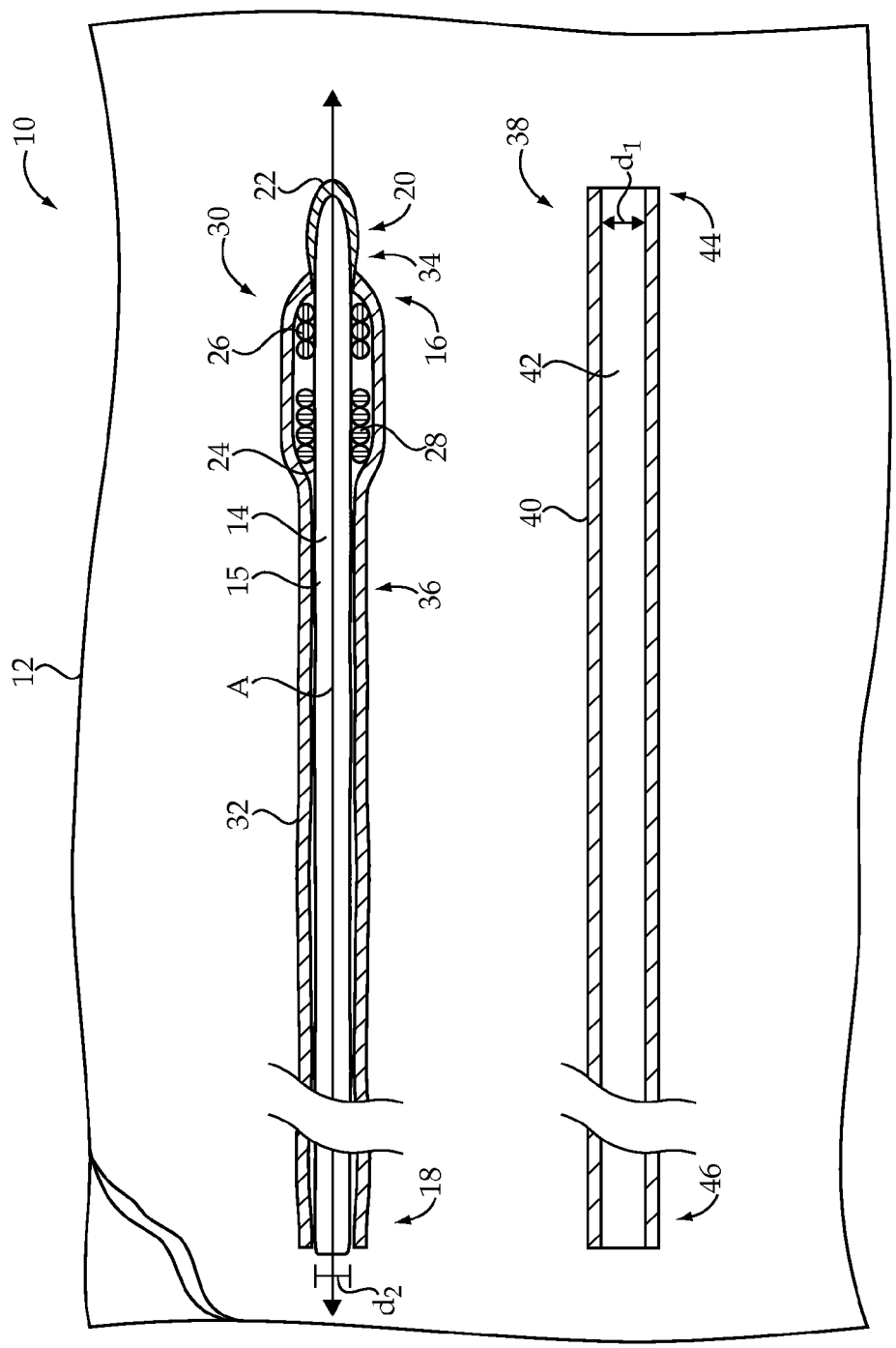
FIG. 1 is a cross sectional schematic of an embolic coil delivery system, according to one embodiment of the present disclosure.

Referring to FIG. 1, there is shown an embolic coil delivery system 10 according to one embodiment of the present disclosure. The embolic coil delivery system 10 may include a number of components, which may be provided within a sterile, tear open package 12, as is known in the art. In performing an embolic coil delivery procedure on a patient, some or all of the components of the embolic coil delivery system 10 may be used, depending upon the specifics of the procedure to be performed. As should be appreciated, however, the components shown in FIG. 1 might be separately packaged and/or the embolic coil delivery system 10 might also include components in addition to those shown, including components routinely used in percutaneous endovascular procedures.

The embolic coil delivery system 10 may generally include a flexible elongate body 14, which may be a solid structure, as shown, or may be hollow, with an outer tube defining an internal lumen. According to the exemplary embodiment, the flexible elongate body 14 may be a mandril wire guide 15 formed from stainless steel, or other commonly selected material, to provide a desired combination of stiffness and flexibility. For example, a certain degree of stiffness may be required for pushability and trackability, while a certain degree of flexibility may be required for improving vasculature navigation. It should be appreciated that the stiffness of the flexible elongate body 14 may be consistent along a longitudinal axis A of the body 14 or may vary, depending on the specifics of the procedure to be performed and the performance characteristics desired.

As shown, the flexible elongate body 14 may include a distal segment 16 that is tapered. The taper, which may increase flexibility of elongate body 14, may be gradual or abrupt, and may begin at any position along the flexible elongate body 14 from a proximal end 18 to a distal end 20 of the body 14. In addition, a thermoplastic polymer coating 22, such as a polyester or polyether block amide, may be provided at the distal end 20 of the flexible elongate body 14. Particularly, the polymer coating 22 may provide a desirable lubricity profile that exhibits low friction during introduction of the flexible elongate body 14 through a vessel of the patient. A coating, such as a thermoplastic coating, may also be provided along an entire length of the flexible elongate body 14. For example, an outer surface 24 of the flexible elongate body 14 may be coated with high density polyethylene (HDPE), polytetrafluoroethylene (PTFE), polyethylene terephthalate (PET), polyester or polyether block amide (PEBA), polyurethane, polyimide, polyolefin, nylon, or any combination thereof. The coatings, including the polymer coating 22, may be applied by, for example, over-extrusion, dip-coating, melt fusion, heat shrinking, or using other known application means.

The embolic coil delivery system 10 may also include a first embolic coil 26 and a second embolic coil 28 loaded on the flexible elongate body 14 at the distal segment 16 of the body 14. Although two embolic coils 26 and 28 are shown, any number of coils, including only one coil, may be loaded on the flexible elongate body 14. The embolic coils 26 and 28 may be helically wound coils, randomly wound coils, coils would within other coils, or may have various other coil configurations. Further, the coils may be made from a radiopaque metallic material, such as, for example, platinum or stainless steel. According to some embodiments, a first stiffness measurement, or durometer, of the first coil 26 may be different than a second stiffness measurement of the second coil 28. The embolic coils 26 and 28, which may have various configurations, may be frictionally engaged with the outer surface 24 of the flexible elongate body 14 to maintain a loaded, or relatively fixed position of the embolic coils 26 and 28 relative to the body 14. The flexible elongate body 14, with the embolic coils 26 and 28 loaded thereon, may also be referenced as a preloaded wire guide 30.

A delivery sheath 32 may be positioned over the embolic coils 26 and 28, as shown in the exemplary embodiment. The delivery sheath 32 may be made from a flexible film, such as, for example, a medical grade polyethylene film, and may be positioned over a segment of the outer surface 24 of the flexible elongate body 24, including the segment supporting the embolic coils 26 and 28. A distal end 34 or, more specifically, an open distal end of the delivery sheath 32 may be removably attached to the flexible elongate body 14 at an axial position of the body 14 that is distally spaced from the embolic coils 26 and 28. Specifically, according to one embodiment, the delivery sheath 32 may have an attached distal end 34 and an unattached proximal end 36 that is unattached relative to the flexible elongate body 14. The unattached proximal end 36, according to the exemplary embodiment, may extend from the attached distal end 34 toward the proximal end 18 of the flexible elongate body 14.

The removable attachment of the delivery sheath 32 to the flexible elongate body 14 at the attached distal end 34 may include any attachment that facilitates removal of the delivery sheath 32, or at least that portion that covers the embolic coils 26 and 28, while the flexible elongate body 14 is positioned within the vasculature of the patient. Thus, the removable attachment may be as simple as a perforated tear away section or may be relatively complex, such as including a repositioning device that may be manipulated externally from the vasculature of the patient. Although a delivery sheath 32 is described, it should be appreciated that another component capable of shielding the embolic coils 26 and 28 and/or maintaining a loaded position of the coils 26 and 28 during an embolic coil delivery procedure may be substituted for the delivery sheath 32.

The embolic coil delivery system 10 may also include a delivery catheter 38 sized to advance over the flexible elongate body 14 during an embolic coil delivery procedure. Specifically, the delivery catheter 38 may include a tube 40 defining an internal lumen 42 extending from a distal segment 44 to a proximal segment 46, wherein the lumen 42 defines an inner diameter $d_1$ that substantially matches an outer diameter $d_2$ of the flexible elongate body 14. As used herein, "matches" means that the inner diameter $d_1$ is slightly greater than the outer diameter $d_2$ or otherwise sized such that the distal segment 44 of the delivery catheter 38 may advance over the flexible elongate body 14 and contact the embolic coils 26 and 28 during an embolic coil delivery procedure. As such, the distal segment 44 may be suitably shaped to urge the coils 26 and 28 from the flexible elongate body 14. The delivery catheter 38 may comprise a lubricious material such as PTFE and may or may not include a reinforcement material to provide kink resistance and torqueability while retaining a desired level of flexibility. As should be appreciated, the delivery catheter 38 may be a multi-layer tube comprised of various other materials, or may even include single polymeric tubes. It should also be appreciated that the materials and overall construction of the delivery catheter 38 and flexible elongate body 14 may be selected to improve or enhance usability of the embolic coil delivery system 10.

INDUSTRIAL APPLICABILITY

The present disclosure is generally applicable to embolic coil delivery systems for use in percutaneous endovascular procedures. More specifically, the present disclosure finds application in procedures to deliver an embolic coil to a delivery site within the vascular system of a patient. Further the present disclosure finds specific application in procedures during which a plurality of embolic coils are delivered to the delivery site within the vasculature of the patient to provide an artificial blockage.

Referring to FIGS. 2-5, an embolic coil delivery procedure using the embolic coil delivery system 10 (FIG. 1) will be described with reference to a vascular structure V of a patient. Although not shown, it should be appreciated that a needle, or introducer, may be used to gain percutaneous access to the vascular structure V, as is known to those skilled in the art. It should also be appreciated that the embolic coils 26 and 28 may be preloaded around the outer surface 24 of the distal segment 16 of the flexible elongate body 14 to define a preloaded wire guide 30. Loading the embolic coils 26 and 28, according to an exemplary embodiment, may include frictionally engaging the embolic coils 26 and 28 with the outer surface 24 of the flexible elongate body 14. Further, a delivery sheath 32, as described above, may be provided over the embolic coils 26 and 28 to shield the embolic coils 26 and 28 during the embolic coil delivery procedure and, particularly, during advancement of the flexible elongate body 14 through the vasculature structure V.

Figure 2:
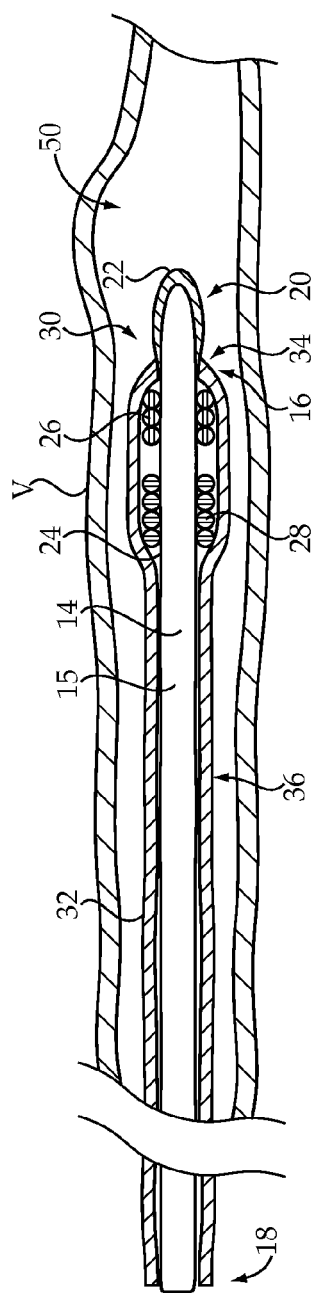
FIG. 2 is a cross sectional schematic of a preloaded wire guide of the embolic coil delivery system of FIG. 1, shown inserted into the vasculature of a patient at a first stage of an embolic coil delivery procedure.

At the first stage of the embolic coil delivery procedure, shown in FIG. 2, the distal segment 16 of the flexible elongate body 14, or preloaded wire guide 30, may be advanced through the vascular structure V to a delivery site 50. The delivery site 50 may represent a desired delivery site for the embolic coils 26 and 28, such as, for example, a bulge or aneurysm. The delivery sheath 32 may assist in maintaining a loaded position of the embolic coils 26 and 28 while the preloaded wire guide 30 is advanced relative to the delivery site 50. It should be appreciated that any of a number of imaging techniques and/or systems may be used to assist in the positioning of the preloaded wire guide 30 or, more specifically, the distal segment 16 of the flexible elongate body 14 relative to the delivery site 50.

Figure 3:
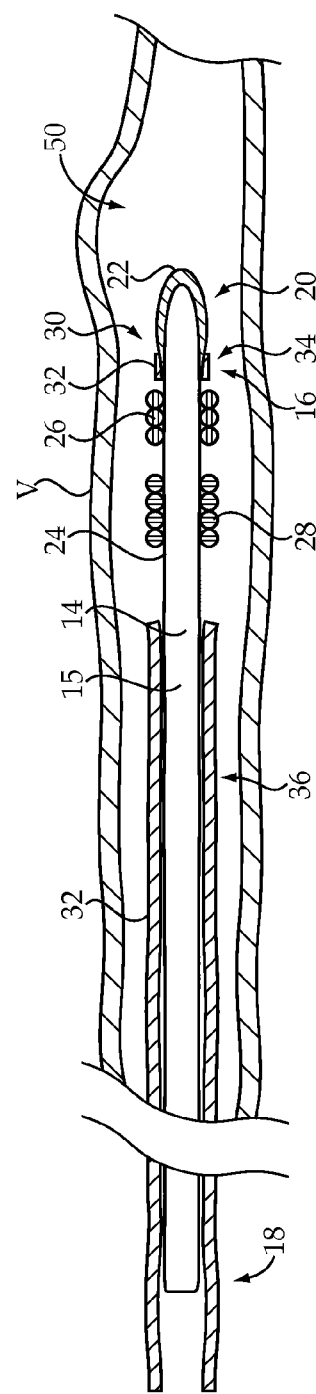
FIG. 3 is a cross sectional schematic of the preloaded wire guide of the previous Figures, shown at a second stage of the embolic coil delivery procedure with a delivery sheath removed.

A next stage of the embolic coil delivery procedure is shown in FIG. 3. Specifically, FIG. 3 depicts the preloaded wire guide 30 positioned such that the distal segment 16 is proximate the delivery site 50. The delivery sheath 32 is also shown partially removed. Removing the delivery sheath 32 may include separating an unattached proximal segment 36 of the delivery sheath 32 from an attached distal end 34 of the delivery sheath 32. For example, a clinician may separate the unattached proximal segment 36 from the attached distal end 34 at a perforated tear away section by pulling, at a location external from the vasculature V, the proximal segment 36 in a proximal direction. In the present disclosure, "proximal" is used to refer to the end of a component or feature that is closest to a clinician or a direction that is toward the clinician, while "distal" is used to refer to a component or feature that is farthest away from the clinician or a direction that is away from the clinician. Such meanings are consistent with conventional use of the terms and, as such, should be understood by those skilled in the art.

Figure 4:
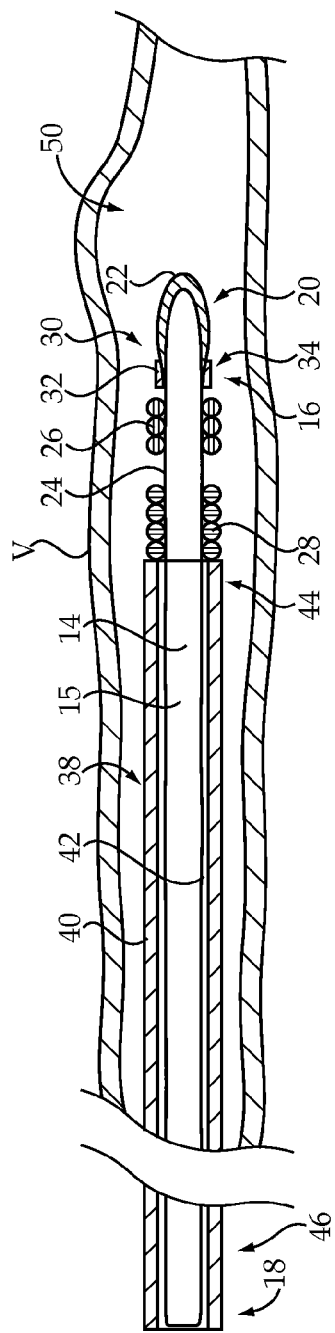
FIG. 4 is a cross sectional schematic of the preloaded wire guide of the previous Figures, shown at a third stage of the embolic coil delivery procedure with a delivery catheter of the embolic coil delivery system advanced over the preloaded wire guide.
Figure 5:
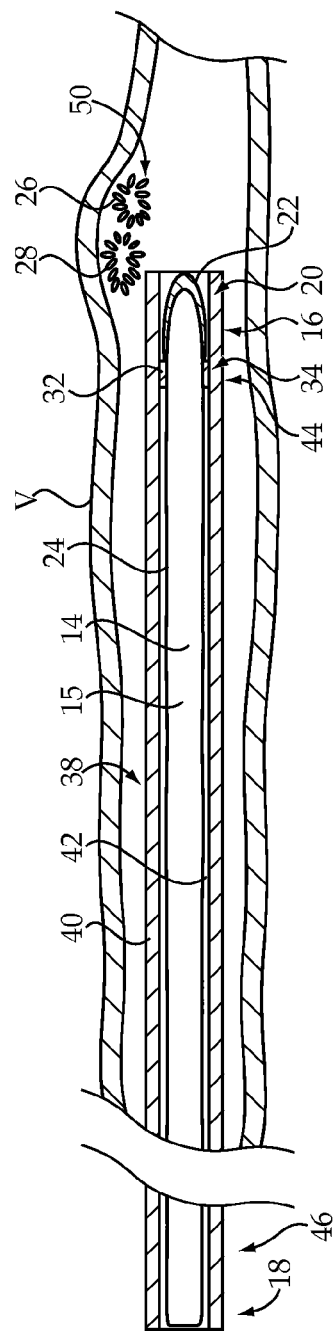
FIG. 5 is a cross sectional schematic of a fourth stage of the embolic coil delivery procedure, wherein the embolic coils are delivered at a delivery site.

Turning now to FIG. 4, the preloaded wire guide 30 is shown with the delivery sheath 32 entirely removed from the flexible elongate body 14. After removing or repositioning the delivery sheath 32, a delivery catheter 38 is advanced over the flexible elongate body 14 such that a distal segment 44 of the delivery catheter 38 contacts at least one of the embolic coils 26 and 28. The embolic coils 26 and 28 may then be unloaded by moving the delivery catheter 38 relative to the flexible elongate body 14 such that the delivery catheter 38 pushes the coils 26 and 28 off of the outer surface 24 of the body 14 at the delivery site 50, as shown in FIG. 5. Once the embolic coils 26 and 28 have been delivered, the remaining components of the embolic coil delivery system 10 may be retracted, or withdrawn, from the vasculature V.

The embolic coil delivery system of the present disclosure provides a system for placement of embolic coil into the vasculature of a patient that can be done in a precise and controlled manner, while maintaining overall simplicity, reliability, and manufacturability. This alternative means for delivering embolic coils does not suffer from the drawbacks of conventional catheter delivery systems relating to resistance provided by the coils loaded into the catheter lumen. As such, the present embolic coil delivery system may be particularly useful in procedures for delivering a plurality of embolic coils.

It should be understood that the above description is intended for illustrative purposes only, and is not intended to limit the scope of the present disclosure in any way. Thus, those skilled in the art will appreciate that other aspects of the disclosure can be obtained from a study of the drawings, the disclosure and the appended claims.

What is claimed is:

1. An embolic coil delivery system, comprising:
    a flexible elongate body having a distal segment;
    an embolic coil loaded on the flexible elongate body at the distal segment and contacting an outer surface of the flexible elongate body;
    a delivery catheter sized to advance over the flexible elongate body during an embolic coil delivery procedure, wherein a distal segment of the delivery catheter contacts the embolic coil during the embolic coil delivery procedure;
    a delivery sheath positioned over the embolic coil, and including a distal end attached to the flexible elongate body; and
    wherein the distal end of the delivery sheath is removably attached to a proximal segment of the delivery sheath at a tear away section located at an axial position of the flexible elongate body distally spaced from the embolic coil;
    wherein the flexible elongate body, the embolic coil and the delivery sheath move together as a unit to a delivery site;
    wherein the embolic coil delivery system has a first configuration in which the embolic coil is covered by the delivery sheath, and a second configuration in which the proximal segment is detached from the distal end of the delivery sheath at a tear away section, and the embolic coil is uncovered and out of contact with the proximal segment.

2. The embolic coil delivery system of claim 1, wherein the proximal segment of the delivery sheath is unattached relative to the flexible elongate body.

3. The embolic coil delivery system of claim 1, wherein the flexible elongate body is a mandril wire guide.

4. The embolic coil delivery system of claim 1, wherein the flexible elongate body, the embolic coil and the delivery sheath have the second configuration in which a proximal segment of the delivery sheath is disconnected from the flexible elongate body and moved proximally to uncover the embolic coil; and
    wherein the embolic coil is frictionally engaged with the outer surface of the flexible elongate body while positioned within the delivery sheath to maintain a relatively fixed position of the embolic coil relative to the flexible elongate body while the flexible elongate body is being maneuvered to the delivery site.

5. The embolic coil delivery system of claim 1, further including a plurality of embolic coils loaded on the flexible elongate body at the distal segment, wherein a first stiffness measurement of a first coil of the plurality of embolic coils is different than a second stiffness measurement of a second coil of the plurality of embolic coils.

6. A preloaded wire guide for an embolic coil delivery system, comprising:
    a mandril wire guide having a distal segment;
    an embolic coil loaded on the mandril wire guide at the distal segment and contacting an outer surface of the mandril wire guide; and
    a delivery sheath positioned over the embolic coil, and including a distal end attached to the mandril wire guide, and the distal end of the delivery sheath is removably attached to a proximal segment of the delivery sheath at a tear away section located at an axial position of the mandril wire guide distally spaced from the embolic coil;
    wherein the embolic coil is frictionally engaged with the outer surface of the mandril wire guide while positioned within the delivery sheath to maintain a relatively fixed position of the embolic coil relative to the mandril wire guide while the mandril wire guide is being maneuvered to a delivery site;

wherein the mandril wire guide, the embolic coil and the delivery sheath move together as a unit to the delivery site;

wherein the embolic coil delivery system has a first configuration in which the embolic coil is covered by the delivery sheath, and a second configuration in which the proximal segment is detached from the distal end of the delivery sheath at a tear away section, and the embolic coil is uncovered and out of contact with the proximal segment.

7. The preloaded wire guide of claim 6, wherein a distal end of the delivery sheath is removably attached to the mandril wire guide at an axial position of the flexible elongate body distally spaced from the embolic coil.

8. The preloaded wire guide of claim 7, wherein a proximal segment of the delivery sheath is unattached relative to the mandril wire guide.

9. The loaded wire guide of claim 8, further including a plurality of embolic coils loaded on the mandril wire guide at the distal segment, wherein a first stiffness measurement of a first coil of the plurality of embolic coils is different than a second stiffness measurement of a second coil of the plurality of embolic coils.

10. The loaded wire guide of claim 9, wherein each of the plurality of embolic coils is frictionally engaged with the outer surface of the mandril wire guide to maintain a relatively fixed position of the embolic coil relative to the mandril wire guide while the mandril wire guide is being maneuvered to the delivery site.

11. A method of delivering an embolic coil to a delivery site within a patient with an embolic coil delivery system that includes a flexible elongate body having a distal segment; an embolic coil loaded on the flexible elongate body at the distal segment and contacting an outer surface of the flexible elongate body; a delivery catheter sized to advance over the flexible elongate body during an embolic coil delivery procedure, wherein a distal segment of the delivery catheter contacts the embolic coil during the embolic coil delivery procedure; a delivery sheath positioned over the embolic coil, and including a distal end attached to the flexible elongate body; wherein a distal end of the delivery sheath is removably attached to the flexible elongate body a proximal segment of the delivery sheath at a tear away section located at an axial position of the flexible elongate body distally spaced from the embolic coil; wherein the flexible elongate body, the embolic coil and the delivery sheath move together as a unit to a delivery site wherein the embolic coil delivery system has a first configuration in which the embolic coil is covered by the delivery sheath, and a second configuration in which the proximal segment is detached from the distal end of the delivery sheath at a tear away section, and the embolic coil is uncovered and out of contact with the proximal segment, and the method comprising steps of:

loading the embolic coil around an outer surface of a distal segment of a flexible elongate body;

advancing the distal segment of the flexible elongate body through the patient vessel to the delivery site with the embolic coil loaded on the distal segment; and unloading the embolic coil from the flexible elongate body at least in part by advancing the delivery catheter over the flexible elongate body and contacting the embolic coil with a distal segment of the delivery catheter; and wherein the embolic coil is frictionally engaged with the outer surface of the flexible elongate body to maintain a relatively fixed position of the embolic coil relative to the flexible elongate body while the distal segment of the flexible elongate body is being maneuvered to the delivery site during the advancing step; and wherein the flexible elongate body, the embolic coil and the- a delivery sheath move together as a unit to the delivery site.

12. The method of claim 11, including shielding the embolic coil with the delivery sheath positioned over the embolic coil prior to and during the advancing step; and wherein the shielding step includes maintaining a loaded position of the embolic coil during the advancing step at least in part by frictionally engaging the embolic coil with the outer surface of the flexible elongate body.

13. The method of claim 11, further including removing at least a proximal segment of the delivery sheath subsequent to the advancing step.

14. The method of claim 13, wherein the removing step includes separating the unattached proximal segment of the delivery sheath from an attached distal end of the delivery sheath along a tear located distal to the embolic coil.

15. The method of claim 11, wherein the loading step includes frictionally engaging the embolic coil with the outer surface of the flexible elongate body to maintain a loaded position of the embolic coil during the advancing step.

16. The method of claim 11, wherein the loading step includes loading a plurality of embolic coils of varying stiffnesses around the outer surface of the distal segment of the flexible elongate body, and the unloading step includes unloading the plurality of embolic coils from the flexible elongate body at least in part by advancing the delivery catheter over the flexible elongate body and contacting at least one of the plurality of embolic coils with the distal segment of the delivery catheter.

* * * * *